United States Patent
Fahl et al.

(10) Patent No.: US 11,690,813 B2
(45) Date of Patent: Jul. 4, 2023

(54) AMINOTHIOL REDUCTION OF ISCHEMIA-REPERFUSION-INDUCED CELL DEATH

(71) Applicant: OBVIA PHARMACEUTICALS LTD, Madison, WI (US)

(72) Inventors: William E. Fahl, Jiangsu (CN); Ningfeng Li, Jiangsu (CN)

(73) Assignee: OBVIA PHARMACEUTICALS LTD, Madison, WI (US)

( * ) Notice: Subject to any disclaimer, the term of this patent is extended or adjusted under 35 U.S.C. 154(b) by 143 days.

(21) Appl. No.: 16/629,851

(22) PCT Filed: Jan. 4, 2019

(86) PCT No.: PCT/CN2019/070444
§ 371 (c)(1),
(2) Date: Jan. 9, 2020

(87) PCT Pub. No.: WO2019/165851
PCT Pub. Date: Sep. 6, 2019

(65) Prior Publication Data
US 2021/0299066 A1    Sep. 30, 2021

Related U.S. Application Data

(60) Provisional application No. 62/710,838, filed on Mar. 1, 2018.

(51) Int. Cl.
*A61K 31/145* (2006.01)
*A01N 1/02* (2006.01)
*A61P 9/10* (2006.01)

(52) U.S. Cl.
CPC .......... *A61K 31/145* (2013.01); *A01N 1/0226* (2013.01); *A61P 9/10* (2018.01)

(58) Field of Classification Search
None
See application file for complete search history.

(56) References Cited

U.S. PATENT DOCUMENTS 6,031,006 A    2/2000   Hausheer et al.

FOREIGN PATENT DOCUMENTS

WO    2017/004485 A1    1/2017

OTHER PUBLICATIONS

Soref et a., A New Orally Active, Aminothiol Radioprotector-Free of Nausea and Hypotension Side Effect at Its Highest Radioprotective Doses. International Journal of Radiation Oncology, Biology, Physics, 2012, 82, e701-707.*
International Search Report issued in corresponding International Application No. PCT/CN2019070444.
Yuan-Wing, Gao et al., "Effect of antioxidant therapy in attenuating liver ischemia/reperfusion injury", Journal of Clinical Rehabilitative Tissue Engineering Research, 13(5): 911-914 (2009, (Eng. abstract only).
Pissarek, M. et al., "Improved Contractile function in the reperfused rat heart by the radical scavenger 2-[3-aminopropylamino] ethane thiol", Biomed. Biochim. Acta., 48(2-3): 126-131 (1989) (Eng. abstract only).

* cited by examiner

*Primary Examiner* — Po-Chih Chen
(74) *Attorney, Agent, or Firm* — Kathleen D. Rigaut; Howson & Howson LLP

(57) ABSTRACT

Members of the PrC-210 family of aminothiols, including PrC-211 and PrC-252, are shown to be highly effective in reducing ischemia-reperfusion injury in two preclinical models, including kidney transplant and myocardial infarct. Compositions and methods employing members of the PrC-210 family of aminothiols are disclosed for suppressing ischemia-reperfusion-induced cell and organ toxicities in a number of settings, significantly including organ transplant and myocardial infarct.

16 Claims, 13 Drawing Sheets

AMINOTHIOL REDUCTION OF ISCHEMIA-REPERFUSION-INDUCED CELL DEATH

CROSS-REFERENCE TO RELATED APPLICATIONS

The present application is a § 371 of International Application No. PCT/CN2019/070444, filed Jan. 4, 2019, which claims the benefit of U.S. Provisional Application No. 62/710,838, filed Mar. 1, 2018.

FIELD OF THE INVENTION

Provided herein is technology in which aminothiol compounds are delivered and contact cells that are exposed to an ischemic event, and in so doing, the aminothiol significantly reduces the severity of the ischemia-reperfusion (I-R) insult to cells. The administered aminothiol reduces several of the steps involved in I-R-induced cell death, including suppression of caspase activation and cellular apoptosis, as well as scavenging of reactive oxygen species (ROS) and reduction of ROS-induced damage to DNA in a host of settings.

BACKGROUND OF THE INVENTION

Lorenzen et al. (*Free Rad. Biol. Med.* July, 2013) summarize the widespread significance of ischemia-reperfusion injury, "tissue damage caused by ischemia-reperfusion (I/R) injury represents a serious event, which often leads to deterioration or even loss of organ function. I/R injury is associated with transient tissue oxygen deprivation due to vessel occlusion and a subsequent reperfusion period following restoration of blood flow. Initial tissue damage inflicted by ischemia is aggravated in the reperfusion period through mechanisms such as a burst of reactive oxygen and nitrogen species and inflammatory reactions. I/R injury occurs during surgical interventions, organ transplantation, diseases such as myocardial infarction, circulatory shock, and toxic insults." Over 21,900 citations are identified when the search term "ischemia-reperfusion" is searched in PubMed, and these examples span virtually every organ site and include both human clinical studies measuring some parameter related to ischemia-reperfusion injury, such as plasma levels of cardiac lactate dehydrogenase during and following myocardial infarct, to levels of lipid peroxidation in brain tissue in rats when a brain artery is clamped for a defined period and then released for a defined period of reperfusion.

Organ transplant provides one example of the significance of I-R-induced cell death and its ramifications. End-stage kidney failure causes greater than 1.2 million deaths annually in the world. Over 17,000 kidney transplants are performed each year in the United States. While short-term outcomes have improved over the last several decades, long-term graft survival has improved only slightly. Much of the kidney graft failure is attributed to I-R injury in the transplanted kidneys (Kloner R A, Circulation. 1989; 80:1115-27). Kidney I-R injury manifests as either primary non-function or delayed graft function. About one-third of all kidney transplants will develop delayed graft function; this failure rate increases to as high as 50% in kidneys donated after circulatory death. Delayed graft function is a well-established risk factor for inferior graft survival. Additionally, delayed graft function leads to increased resource utilization and expense in the immediate post-transplant setting as one awaits the return of kidney function. As a result, an important, unmet need in solid organ transplantation is the prevention of I-R injury. Significantly, organ preservation strategies, which could reduce I-R injury, have not significantly changed over the last 50 years. Thus, there is a major, unmet need in the field of kidney transplantation for new, safe, and effective means to suppress I-R injury to transplanted kidneys, with the ultimate goal of achieving life-long graft survival. Successful suppression of I-R injury in kidney transplant could be broadly applied to other transplanted organs, and more so, broadly applied to all organ surgeries where blood supply is interrupted during surgical manipulation, and then re-established, this includes all coronary bypass, open-heart, and neural surgeries.

The complete mechanisms underlying I-R injury are complex and incompletely understood, but oxidative stress, caspase activation, cell apoptosis, ATP depletion and calcium dyshomeostasis all contribute to the mechanism and are all broadly recognized as the cause of I-R injury (Weight S C, *Br J Surg,* 1996; 83:162-70). The generation of reactive oxygen species (ROS) in the reperfusion phase leads to DNA mutation. Apoptotic death cascades are initiated, ultimately leading to cell death. In organ transplant alone, suppressing I-R injury would improve outcomes in transplant surgeries and decrease acute and chronic rejections in all organ transplants.

Like organ transplant, ROS generation, caspase activation and apoptotic death cascades are as common in myocardial infarct and reperfusion as they are in virtually all models of organ toxicity that are precipitated either experimentally or in nature by organ ischemia/infarct followed by removal of the infarct to enable reperfusion of the organ with oxygenated blood.

Following is a small sample of examples of ischemia-reperfusion injury, from a PubMed search of ischemia-reperfusion injury to various organs, and examples of how pre-administration or co-administration of a thiol served to reduce the severity of the ischemia-reperfusion damage to the at-risk tissue.

TABLE 1

Published Literature Showing Protective Effects of Some Existing Thiols

| Ischemia-Reperfusion Organ Toxicity Tested | ROS-Scavenger Tested | Lead Authors |
| --- | --- | --- |
| Rabbit spinal cord injury | amifostine | F Chronidou |
| Rat kidney | amifostine | MK Chok |
| Mouse Heart | amifostine | SZ Wu |
| Rat liver transplantation | NAC* | SM Silva |
| Rat lung hemorrhagic shock | NAC | KR Saad |
| Rat testicular injury | NAC | STurkmen |

*N-acetylcysteine

The thiol compounds amifostine, cysteamine and N-acetylcysteine have been shown to have discernible protective effect in certain animal models of ischemia-reperfusion organ damage. In two of the Table 1 cited cases (MK Chok; SZ Wu), systemic amifostine administration was shown to have effects on caspase 3 expression as well as anti-apoptotic effects.

However, each of the thiols in Table 1 have significant pharmacologic shortcomings, that significantly limit, and in the case of amifostine/WR-1065 preclude, their use in clinical settings. For instance, amifostine causes severe nausea/emesis side effects as well as hypotension/fainting side effects in humans. The amifostine active metabolite WR-1065 shows hypotension side effects in rats (Ryan, 1996), and though not published to date, to our knowledge, WR-1065 is also likely to induce the nausea/emesis response strongly associated with amifostine administration. N-acetylcysteine is an odorous compound of limited activity that primarily acts indirectly as a GSH precursor and is thus slower acting. It can cause severe adverse reactions ranging from nausea to death (Sandilands, 2009). Vomiting (Pakravan, 2008) and anaphylactoid reactions (Kao, 2003) are seen frequently. Thus, there is a need for a new agent that can be developed into an applicable pharmaceutical product to protect a subject from ischemia-reperfusion cell death which both lacks the nausea-emesis and hypotension side effects of amifostine/WR-1065 that preclude their clinical use and has greater clinical efficacy.

OBJECTS AND SUMMARY OF THE INVENTION

The inventors have found, in part through the Examples provided herein, that the compounds of this invention avoid many or all of the shortcomings described with previous aminothiols such as amifostine and WR-1065, which makes the molecules of this invention fundamentally better suited for widespread use in human populations to provide protective and therapeutic benefit in a diverse set of medical applications. Significantly, this includes profound suppression of caspase/apoptosis in kidney transplant (Examples 3-5) as well as apoptosis/cell death in myocardial infarct (Example 6).

It is found that the molecules of this invention can suppress ischemia-reperfusion injury (see Examples 3, 4, 5 and 6) without causing nausea/vomiting (see Example 10) and hypotension/fainting (see Example 11) side-effects which have greatly restricted the use of the current generation aminothiol, i.e., the five carbon aminothiophosphonate pro-drug, amifostine. The design concepts of the aminothiols used in the invention are: (i) a flexible alkyl chain backbone, which carries positive charge(s) at pH 7.2 due to one or more amine groups to achieve ionic interaction with and to concentrate around the negatively charged DNA in cells, and (ii) the presence of a free thiol group to scavenge oxygen free radicals formed during ischemia-reperfusion.

In the original design of this new family of aminothiols, PrC-210 serving as the best characterized prototype to date, we explored a process in which: (i) the number of alkylamine segments in the aminothiol backbone was systematically increased to increase drug-DNA affinity and ionic interaction, resulting in increased growth inhibition that is associated with this enhanced drug-DNA interaction, and (ii) the placement or 'display' of a free thiol ROS scavenger at the end of an alkyl side chain that displaces or 'displays' the scavenger moiety away from the DNA backbone to enable ROS scavenging before the ROS attack dG bases within cellular DNA (see FIG. 1 schematic). This work has resulted in a family of new aminothiol molecules, which includes PrC-210, PrC-211, and PrC-252.

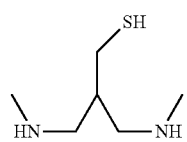

PrC-210

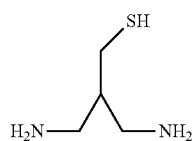

PrC-211

PrC-252

The prototype PrC-210 is described in detail here. These compounds, in particular PrC-210, do not show the disadvantages seen for prior art compounds, such as amifostine, WR-1065, N-acetylcysteine, or cysteamine. The present compounds show high efficacy and rapid onset of action. They cause neither nausea nor hypotension, and they are nearly odorless.

Aminothiol Chemistry:

Structures of the aminothiols used in this invention to suppress caspase and apoptosis, and scavenge ROS as means, among others, to reduce I-R injury include the following:

wherein A=—CH$_2$NHR' and B=—CH$_2$NHR or A=—NRR' and B=H; and wherein R and R' are independently selected from H, alkyl, and heteroalkyl, with the proviso that R and R' are not both H if B=H, and pharmaceutically acceptable acid addition salts thereof.

Alkyl preferably means C$_1$-C$_6$ alkyl, in particular C$_1$-C$_3$ alkyl and especially methyl. Heteroalkyl preferably means C$_1$-C$_6$ heteroalkyl, in particular C$_1$-C$_3$ heteroalkyl and especially C$_1$-heteroalkyl.

Preferred compounds are those having the following formula:

wherein R and R' are independently selected from H, alkyl, and heteroalkyl, and pharmaceutically acceptable acid addition salts thereof. Alkyl preferably means C$_1$-C$_6$ alkyl, in particular C$_1$-C$_3$ alkyl and especially methyl. Heteroalkyl preferably means C$_1$-C$_6$ heteroalkyl, in particular C$_1$-C$_3$ heteroalkyl and especially C$_1$-heteroalkyl.

Further preferred compounds are:

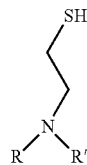

wherein R and R' are independently selected from H, alkyl, and heteroalkyl, with the proviso that R and R' are not both H, and pharmaceutically acceptable acid addition salts thereof. Alkyl preferably means $C_1$-$C_6$ alkyl, in particular $C_1$-$C_3$ alkyl and especially methyl. Heteroalkyl preferably means $C_1$-$C_6$ heteroalkyl, in particular $C_1$-$C_3$ heteroalkyl and especially $C_1$-heteroalkyl.

Particularly referred compounds are PrC-210, PrC-211, and PrC-252 and pharmaceutically acceptable acid addition salts thereof. Especially preferred is PrC-210 or pharmaceutically acceptable acid addition salt thereof, such as the hydrochloride.

The molecules indicated above, as well as analogs of these molecules, are synthesized using routes that we have previously described (U.S. Pat. No. 7,314,959; Copp, R R et al., Synthesis and Growth Regulatory Activity of a Prototype Member of a New Family of Aminothiol Radioprotectors. Bioorganic Medic. Chem. Letters 21:7426-7430, 2011).

A brief summary of why the compounds used in the present invention, in particular the PrC-210 aminothiol, are better suited to reduce I-R injury than other thiols or aminothiols that are currently available, includes:

1. The present compounds and in particular PrC-210 and its PrC-211 and PrC-252 analogs are very effective in suppressing apoptosis-associated caspase levels in both mouse kidneys and mouse hearts that have experienced a 30 min (kidney) or 40 min (heart) I-R insult (Examples 3-6).
2. PrC-210 is an extremely efficient in vitro ROS-scavenger (see Examples 1 and 2).
3. PrC-210 is a potent ROS-scavenger, in both in vitro (Eppendorf tube; Examples 1 and 2) and primary mouse cardiomyocyte (Example 7) settings. At ~3 mM concentration, PrC-210 can suppress DNA damage (pUC19 DNA damage, see FIG. 2) by 90%; and 3 mM is the same PrC-210 thiol blood concentration that we measured (Example 15) in mice that received the 0.5 MTD dose of PrC-210 (i.e., 252 µg/gm b.w.), which conferred 100% survival to mice against an otherwise 100% lethal dose of radiation; death in these mice occurs primarily from the cellular ROS formed secondary to the ionizing radiation.
4. PrC-210 is designed to contain an alkyl side chain that displays a thiol group at least three bond-lengths away from the DNA backbone with which the PrC-210 alkyl-amine backbone ionically associates. We postulated that displacing the thiol into the milieu surrounding the DNA backbone would enable more efficient ROS-scavenging before the ROS could attack dG bases within the DNA backbone.
5. The PrC-210 molecule does not induce a hypotension response, unlike amifostine. This means PrC-210 can be used in unsupervised patients in an out-clinic setting. Also, it implies that PrC-210 can be used in patients in critical care settings like myocardial infarct, stroke or coronary bypass surgery settings without significantly increasing required patient oversight. It is believed that this also applies to the other compounds used in the present invention.
6. The PrC-210 molecule does not induce any retching or emesis response, unlike amifostine. This means PrC-210 can be used in unsupervised patients in an out-clinic setting. Also, it implies that PrC-210 can be used in patients in critical care settings like myocardial infarct, stroke or coronary bypass surgery settings without significantly increasing required patient oversight. It is again believed that this also applies to the other compounds used in the present invention.
7. The compounds of the present invention do not have an objectionable odor. PrC-210 is essentially free of sulfurous odor (see Example 12). This is unlike the thiols N-acetylcysteine and cysteamine, both of which have shown little or modest efficacy in suppressing ischemia-reperfusion injury, but which remain clinically unusable in humans because of the pervasive smell associated with their use at clinically relevant doses.
8. Amifostine requires an enzymatic activation step by a phosphatase to become a free thiol, and this has an associated time-dependent pharmacokinetics associated with it. N-acetylcysteine (NAC) achieves the majority of its protective efficacy by augmenting biosynthesis of the endogenous thiol, glutathione, so there is a longer (hours to a day), time-dependent element associated with NAC suppression of ischemia-reperfusion injury. In contrast to these compounds, the present compounds, are fast-acting. They are active the second when they enter the bloodstream, organ preservation solution, or any site in which they are administered. Having the functionally-active, fast-acting compound delivered into the circulatory system during a myocardial infarct, stroke or other cardio- and/or vascular events/conditions, with some delivery around the infarct and a bolus of delivery upon dissolution of the infarct, could be extremely useful in mitigating infarct-associated organ damage.

For protection of transplanted organs against the I-R insult encountered during the transplant-associated blood stop and start, a compound used in the present invention, such as PrC-210, can be administered in one, or in multiple overlapping ways, to protect the organ. Its primary use will be as an additive to the organ preservation solution. Typically, this will involve flushing the donor organ with a solution augmented with a compound used in the present invention, such as PrC-210. The solution used for flushing the donor organ may be one of the commonly used organ preservation solutions augmented with a compound used in the present invention, such as PrC-210. The composition of a commonly used organ preservation solution, "UW Solution," is provided in Example 14; other preservation solutions are known in the art. The donor organ may also be flushed with any other suitable solution, augmented with one or more compounds used in the present invention, such as PrC-210. For instance, the donor organ may be flushed with Lactated Ringer's Solution with albumin and heparin A suitable concentration of the compound used in the present invention will be chosen based on the half-life of the compound and will accommodate different organs (kidneys, hearts, lungs, etc.), storage temperatures, and importantly, the duration of organ storage at 4° C. prior to implant into the organ recipient. For instance, based upon the 3.5 hr half-life of PrC-210 at pH 7.2, the range of aminothiol added could vary between 5-100 mM.. "Flushing" the donor organ with the augmented preservation solution can take several forms, most typically the surgeon simply flushing the removed organ until the organ effluent "runs clear." It can also involve systematic replacement of the entire donor's blood volume, once the donor is pronounced dead, with the organs in situ, with the augmented preservation solution. This latter approach enables flushing and donation of multiple organs from the same donor.

The isolated organ can also be maintained with the augmented preservation solution, buffer, blood or blood substitute continuously circulated through the organ by pump prior to organ implant.

Because the donor organ can often be in storage for 5-8 hours or more before implant, a significant proportion of the compound used in the present invention may be converted to an inactive form during storage of the organ. For instance, in case of PrC-210, 1-2 half-lives or more of PrC-210 conversion to its inactive disulfide form could occur prior to organ implant and the well-known burst of ROS that is associated with newly implanted organs when blood flow is re-established. For this reason, a "loading dose" can be administered to the organ minutes before surgical implant of the organ into the recipient patient. Concentrations of the compound used in the present invention in the loading dose liquid can vary between 5 and 500 mM depending on the organ and its internal circulation. Surgeons can flush the organ using a 50-100 cc syringe and simply push the augmented solution into the organ's primary artery. After waiting a few minutes, a second flush with saline or lactated Ringer's solution alone, just prior to implant, could achieve "loading" of the organ's parenchymal cells with the compound used in the present invention while greatly reducing the amount of this compound that distributes into the organ recipient's systemic blood after implant.

Because it is known in the art that sustained inflammation, with associated ROS, caspase and apoptosis production, persist in newly transplanted organs, it will also be beneficial to administer the compound used in the present invention, such as PrC-210 systemically to patients for 18 hours-4 days after completion of the organ transplant surgery. We know from animal studies that PrC-210 blood concentrations of 1-3 mM are seen in rodents that are protected against organ cell death. Thus, a blood concentration target of the compound used in the present invention for post-transplant organ recipients would be in the 0.5-5 mM range. Administration of the compounds used in the present invention to the patients can be by intravenous or oral administration. For PrC-210 both routes have been shown to be effective in animal studies (Soref, C, Int J Rad Onc Biol Phys 82:e701-e707, 2012).

Previous work has shown that PrC-210, when stored as dry crystalline material in an air-evacuated vial, is stable in its thiol form for several years. When dissolved in pH 6 water, there was no discernible conversion of PrC-210 to its disulfide form over two weeks at room temperature. At pH 7.2, the half-life of the PrC-210 thiol is 3.5 hr. In this context, storage of the compound used in the present invention, such as PrC-210, as crystals or lyophilized powder in a vial flushed with an inert gas, such as nitrogen that is reconstituted with saline and then added to preservation solution or an IV bag would be appropriate. A capsule form of the compound used in the present invention in an inert gas-flushed bottle, such as a nitrogen-flushed bottle would be another way to stably store the molecule prior to administering the capsule orally to a patient, or dissolving a capsule in a defined volume of preservation solution or buffer prior to flushing and preserving isolated organs.

For the large majority of heart surgeries, blood flow is first diverted to a mechanical heart-lung machine, and the heart is then flushed with a chilled cardioplegia solution where the ion content of the solution is designed to prevent spontaneous beating of the isolated heart. The formulation of a standard cardioplegia solution is shown in Example 13. The isolated, non-beating heart is then surgically manipulated during, such as, coronary bypass or valve repair surgery. A cardioplegia solution augmented with the compound used in the present invention, such as PrC210, would protect the heart parenchymal cells against the bolus of ROS and associated caspase and apoptosis that is known to occur in hearts immediately following restoration of oxygenated blood flow to the heart, for instance, following coronary bypass surgery. The augmented cardioplegia solution may contain 5-500 mM of the compound used in the present invention, such as PrC-210. Additional chronic intravenous administration (18 hours-4 days) of the compound used in the present invention, such as PrC-210 to the post-surgical heart patient would also be a useful option.

There are countless other ischemia-reperfusion injury settings, which do not include surgical intervention, where systemic administration (typically by IV) of a compound used in the present invention, such as PrC-210 would reduce the severity of the I-R insult. Because, as a bolus of ROS was generated in a newly-reperfused tissue, the blood-borne compound would provide real-time scavenging of the generated ROS (see Example 2) and thus greatly reduce the associated caspase and apoptosis generation in the post-IR insult tissue setting. Two examples of these non-surgical, IR insult settings include: i) heart attack and release of the myocardial infarct by angioplasty or coronary bypass surgery (see Example 6 for a mouse model recreation of this and the significant reduction in heart cell death associated with PrC-210 systemic administration), and ii) stroke and its catheter or pharmacologic resolution. In these aforementioned embodiments, some of the systemically administered compound will pass or "leak" around the circulatory obstruction; this will enable i) the compound scavenging of reactive molecules (e.g., nitrous oxide) within the ischemic tissue, and ii) the compound scavenging of the bolus of ROS that is formed upon re-established blood flow to the formerly ischemic tissue. In these non-surgical IR insult settings, the compound will most likely be given as an acute, intravenous infusion at a high enough concentration to achieve therapeutic systemic blood levels of 1-20 mM of the compound in seconds/minutes.

In all PrC-210 and related analog formulations, the aminothiol is synthesized (Copp, R Bio Med Chem Lett 21:7426-7430, 2011) as an organic acid salt (typically HCl) and it dissolves virtually instantly in aqueous solutions at up to multi-molar concentrations.

Additional embodiments of this invention will be apparent to persons skilled in the art based on the teachings contained herein.

EXAMPLES

Example 1

Figure 1:
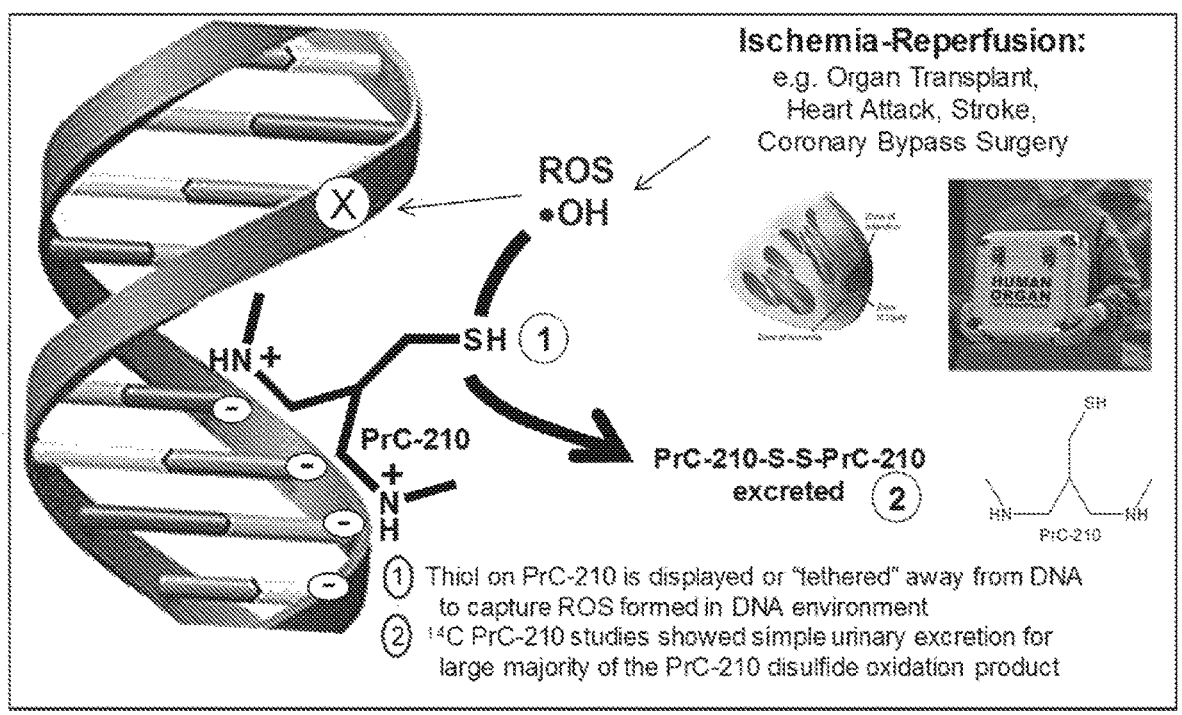
FIG. 1 shows a schematic for one of the proposed mechanisms of protection conferred by PrC-210 against ischemia-reperfusion injury to cells.
Figure 2A:
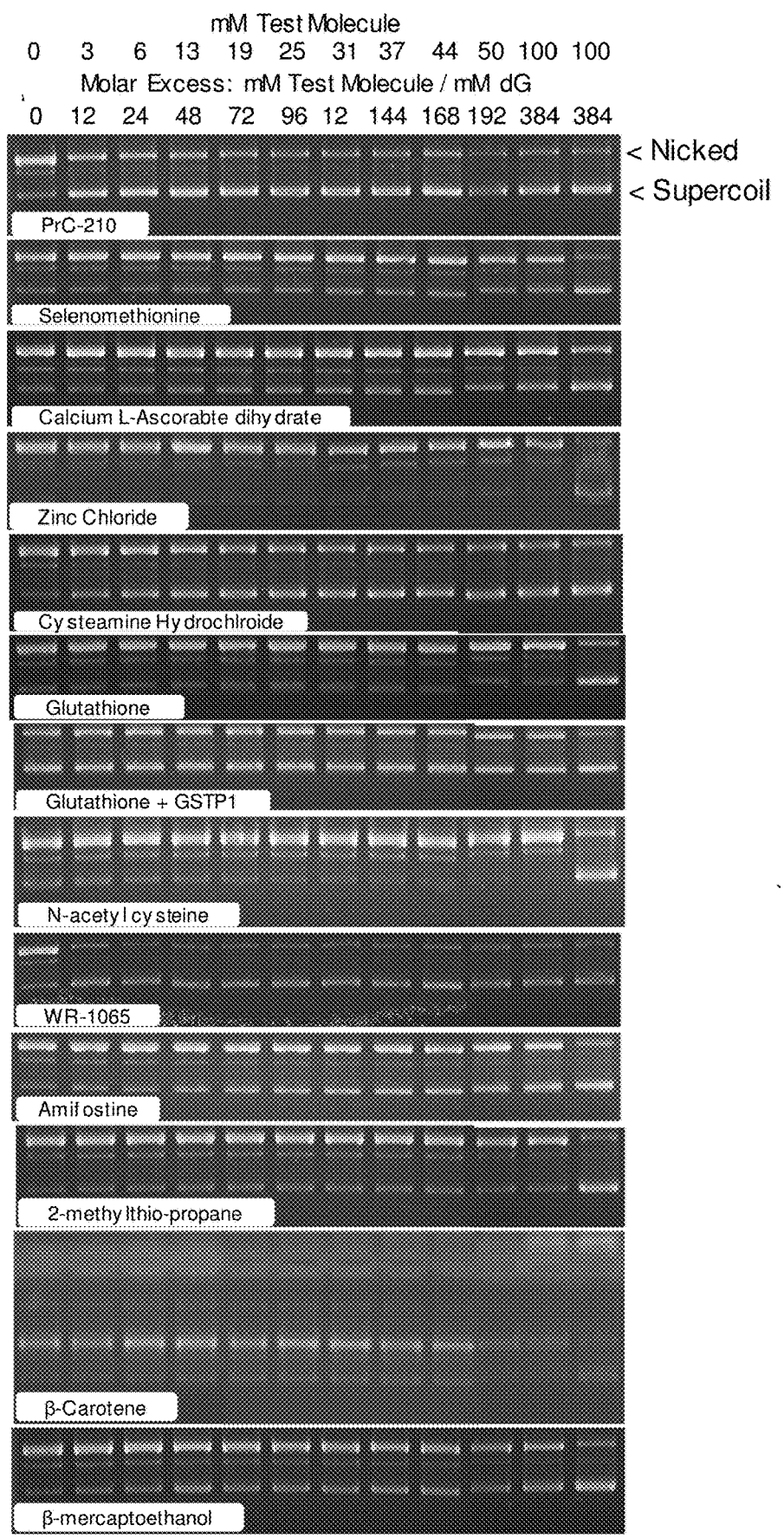
FIG. 2 shows the efficacy of PrC-210 versus 12 commonly cited "antioxidants" in their dose-dependent ability to suppress hydroxyl radical (—OH)-induced nicking of pUC19 plasmid DNA when added to the reaction.
Figure 2B:
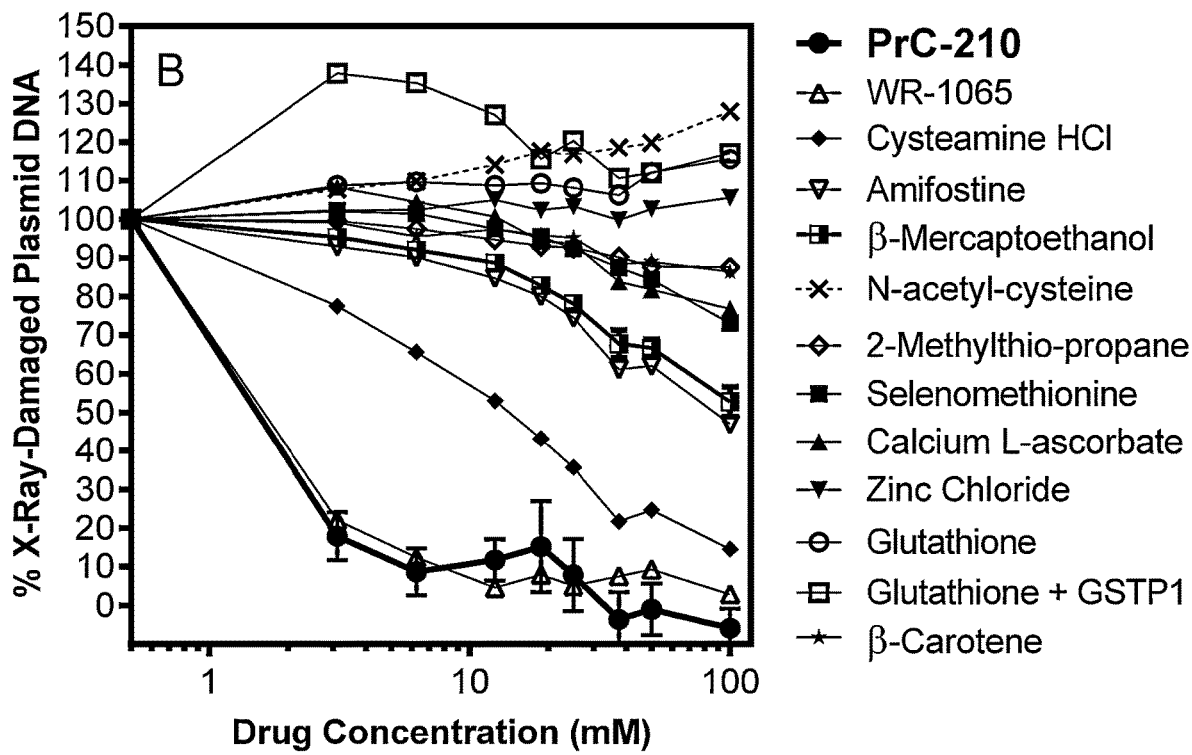
Figure 2C:
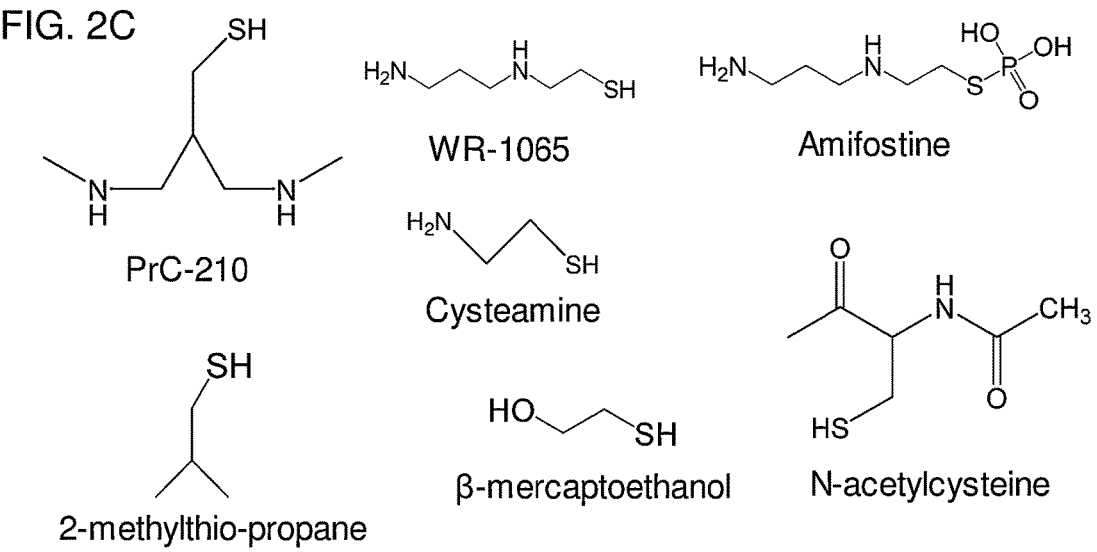

During the development of embodiments of the technology provided herein, experiments were conducted demonstrating that pUC19 plasmid can be separated on an agarose gel to show both the supercoiled form (Supercoil) and the nicked (Nicked) form (FIG. 2, Panel A). As shown in the results, when one or more bonds within the supercoiled plasmid DNA backbone are broken by chemical attack from the reactive oxygen species (ROS) generated during x-irradiation to the plasmid DNA, the supercoiled plasmid DNA is changed into a nicked form and can be separated from the supercoiled plasmid DNA on the agarose gel during electrophoresis. In this Example, the ROS generated during x-irradiation are simply mimicking the same ROS species that are formed during a standard ischemia and reperfusion cycle. ROS-attack on the naked plasmid DNA results in a relaxed plasmid form that migrates more slowly on the gel. In this Example, the indicated small molecules were individually added to plasmid tubes 15 min prior to x-irradiation to determine what protection, if any, they conferred against the bolus of ROS generated during x-irradiation. 15 min after test molecules were added to pUC19 plasmid incubations, tubes received 90 Gy of radiation over 30 min. (A) Aliquots of incubations were then electrophoresed and quantitative imaging of ethidium bromide stained gels was done. Intensities of lower (supercoiled) and upper (nicked) bands were quantified using Image J software. (B) Band intensities were plotted using Graphpad Prism software. (C) Structures of some of the tested molecules are shown. Addition of PrC-210, WR-1065 or cysteamine to the incubations each conferred dose-dependent suppression of the ROS-induced damage to the plasmid DNA.

Example 2

Figure 3:
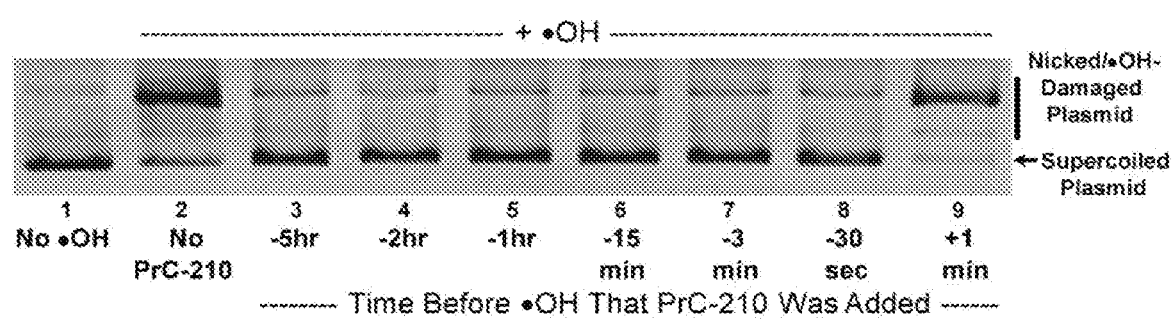
FIG. 3 shows complete prevention of .OH-induced pUC19 plasmid damage when PrC-210 is added to the reaction mixture as little as 30 seconds before generating the .OH insult.

These experiments show the agarose gel separation (FIG. 3) of supercoiled and nicked/.OH-damaged forms of pUC19 plasmid DNA after exposure of plasmid DNA to a 60 sec pulse of an .OH generator ($H_2O_2$+UV light; Floyd et al., J Biochem Biophys Methods 1984; 10:221-235). Supercoiled DNA was incubated with water (lanes a, b) or 20 mM PrC-210 (lanes c-h) for the indicated times and then exposed for 1 min to the .OH generator. Aliquots of each reaction were electrophoresed, stained with EtBr and digitally imaged. Three replicate reactions and gels were done, and band intensities were quantified using Image J software. P value for comparison of supercoiled band intensities in lanes a vs g is indicated. Addition of PrC-210 as little as 30 seconds before the .OH insult conferred complete suppression of ROS DNA damage.

Example 3

Figure 4:
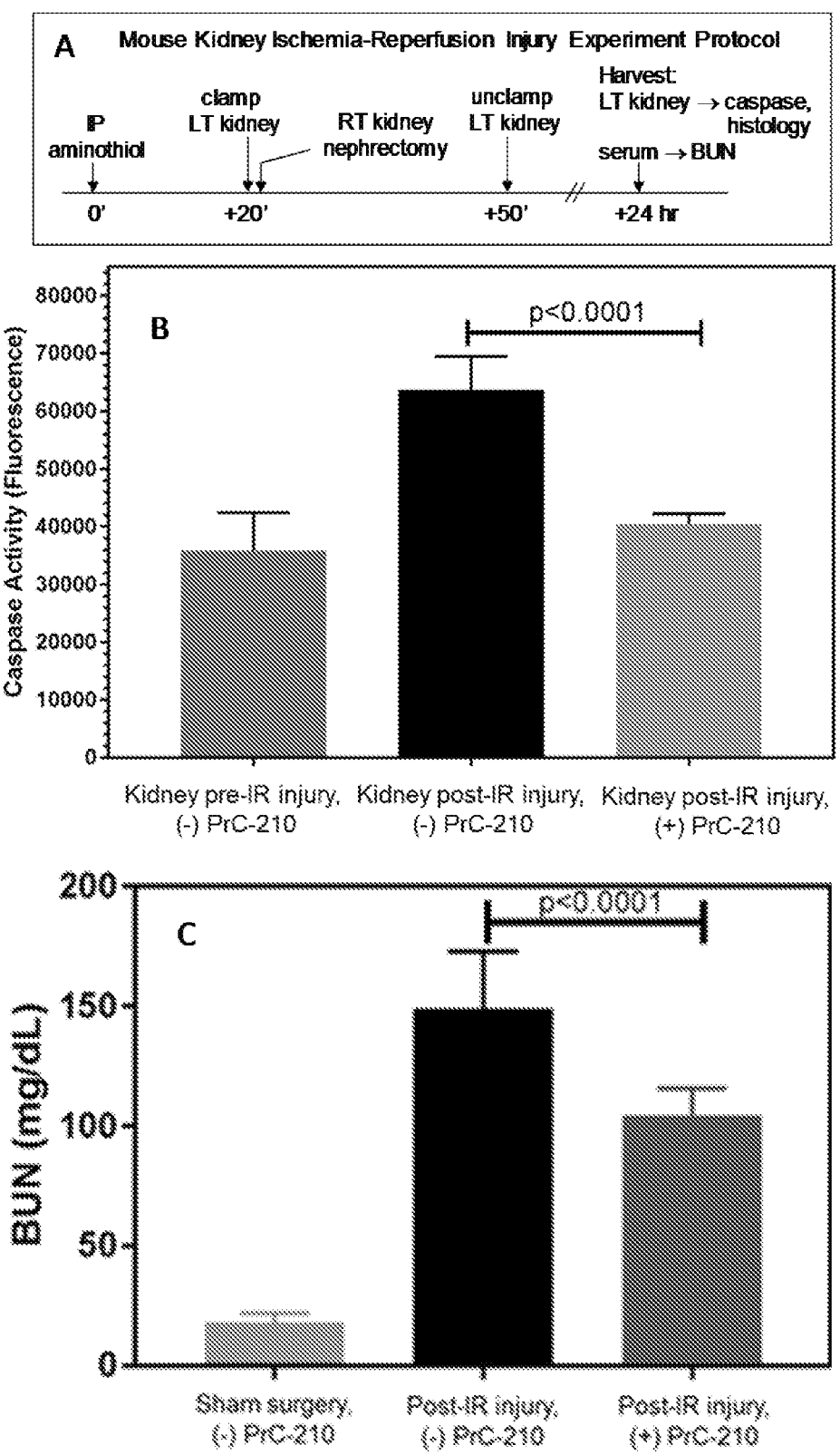
FIG. 4 shows the effects of PrC-210 on renal caspase and renal function 24 hr after mouse renal I-R injury. (A) Experimental design; all groups underwent 30 min of left (LT) ischemia (clamp) and right (RT) nephrectomy followed by 24 hr of reperfusion. Aminothiol (PrC-210, PrC-211 or PrC-252) was administered as a single intraperitoneal (IP) injection 20 min before LT kidney clamp. Serum and LT kidney were harvested at 24 hr. (B) Kidney tissue supernatant caspase activity was measured as described in Example 3. Linearity of the caspase assay conditions over 60 min were first established. (C) BUN levels were determined on serum harvested 24 hr post-clamp.

Experiments were conducted demonstrating (FIG. 4) that administering a single IP injection of PrC-210 (0.24 MTD=0.116 mg/gm body weight) caused an 84% reduction in the level of kidney caspase 24 hr after the I-R insult to the kidney, and a like reduction in serum blood urea nitrogen (BUN) level. (A) Experimental design; all groups underwent 30 min of left (LT) ischemia (clamp) and right (RT) nephrectomy followed by 24 hr of reperfusion. PrC-210 was administered as a single intraperitoneal injection 20 min before LT kidney clamp. Serum and LT kidney were harvested at 24 hr. (B) Kidney supernate caspase activity was measured as follows: Caspase 3 and 7 activity in kidney homogenate supernates was determined using the Apo-ONE fluorescent substrate (Promega, Madison, Wis.). Briefly, thawed kidneys were mixed with an 8-fold excess of lysis buffer containing 50 mM Na HEPES, pH 7.4, 100 mM NaCl, 1 mM EDTA, 10 mM DTT, 10% glycerol and homogenized at 4° C. for 30 sec with a stainless steel blade homogenizer (5,000 rpm). The kidney homogenate was then centrifuged at 4° C. at 16,000×g in an Eppendorf 5418 microfuge for 20 min. The resultant supernates were immediately frozen and stored at −70° C. Supernate protein was measured by the Bradford method using bovine serum albumin standards. The caspase assay was performed as follows: 38 μg of supernate protein diluted to a total volume of 50 ul with the above lysis buffer, was mixed with 50 μL of the Apo-ONE substrate in the well of a black 96 well plate to initiate the 60 min reaction. Plates were shaken at 200 rpm at 37° C. for 60 min. The DEVD caspase substrate peptide cleavage was measured using a BMG Clariostar fluorescent plate reader at an excitation wavelength of 499 nm and an emission wavelength of 521 nm. A caspase standard was included for each experiment. (C) BUN levels were determined on serum harvested 24 hr post-clamp as a functional indicator of kidney health over the 24 hr following the I-R insult.

Example 4

Figure 5:
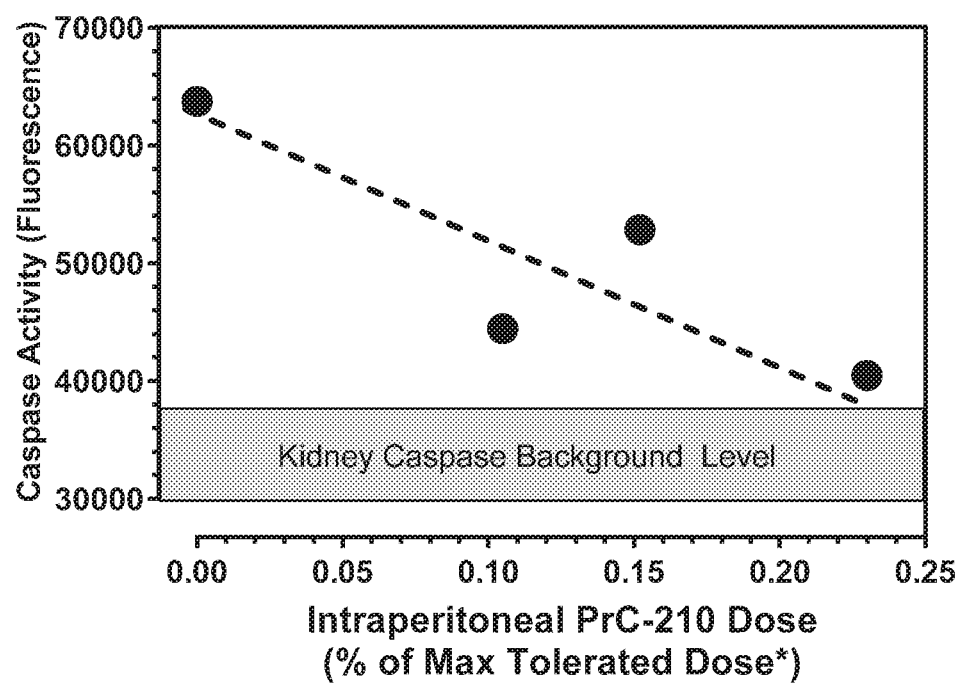
FIG. 5 shows the dose-dependent PrC-210 suppression of left kidney caspase activity 24 hr post-clamp. PrC-210 doses were administered as a single IP injection 20 min before clamp, and caspase activity was measured 24 hr later. PrC-210 doses are indicated as fractions of the IP maximum tolerated dose (MTD) determined previously on wild-type mice, which is 504 ug/gm body weight (b.w.).

Experiments were conducted demonstrating (FIG. 5) that administering single IP injections of PrC-210, at a range of three doses (0.105 MTD, 0.152 MTD, 0.230 MTD=0.053, 0.077, 0.116 mg/gm body weight, respectively) caused a PrC-210 dose-dependent reduction in the level of kidney caspase measured 24 hr after the I-R insult to the kidney.

Example 5

Figure 6:
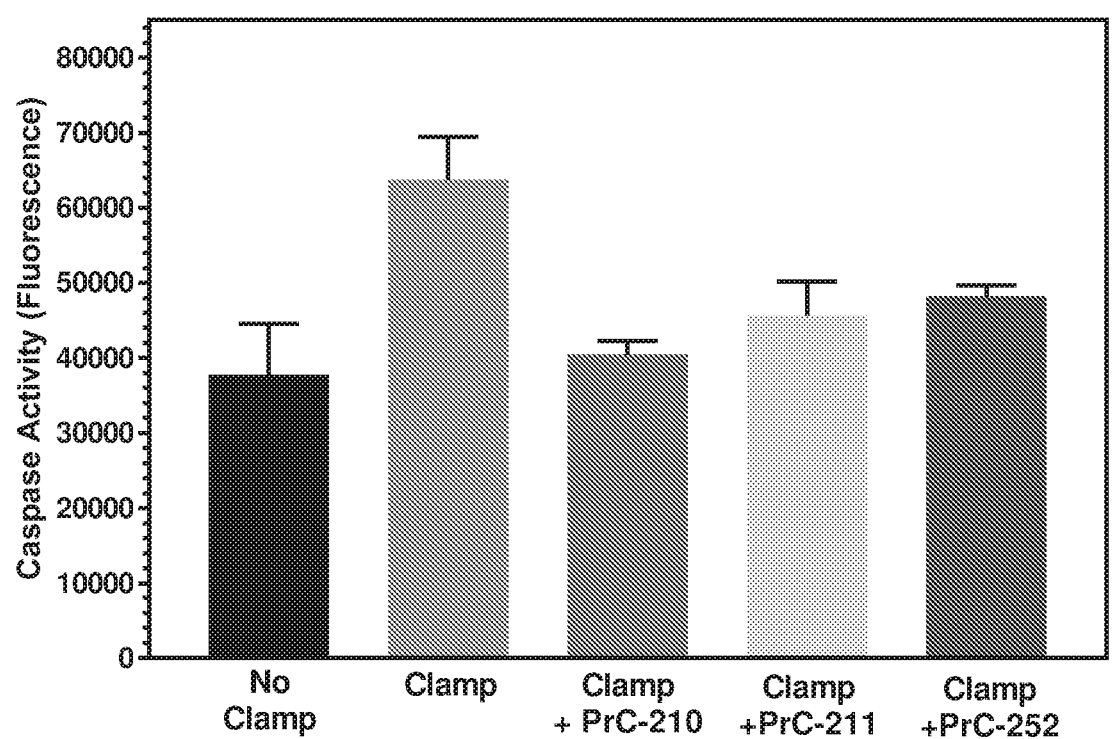
FIG. 6 shows the ability of each of the indicated aminothiols (and their structures) to reduce the level of kidney caspase 24 hr after the 30 min I-R insult to the kidney. A 0.24 MTD dose of each aminothiol was administered as a single intraperitoneal injection to mice 20 min before the 30 min clamp of the left kidney was initiated. Kidneys were harvested 24 hr later and assayed for caspase activity.
Figure 6:
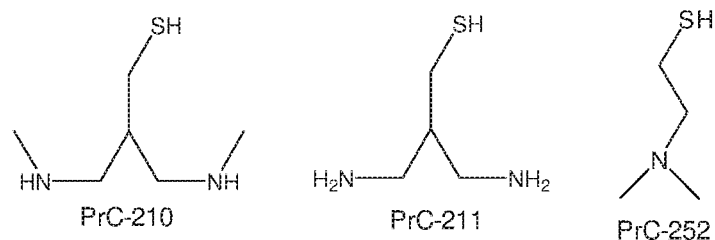

Experiments were conducted demonstrating (FIG. 6) that administering a single IP injection of PrC-210, PrC-211 or PrC-252 at their respective 0.24 MTD doses (PrC-210 MTD=504 ug/gm body weight; PrC-211 MTD=500 ug/gm body weight; PrC-252 MTD=287 ug/gm body weight) caused highly significant reductions in the level of kidney caspase measured 24 hr after the I-R insult to the kidney.

Example 6

Figure 7:
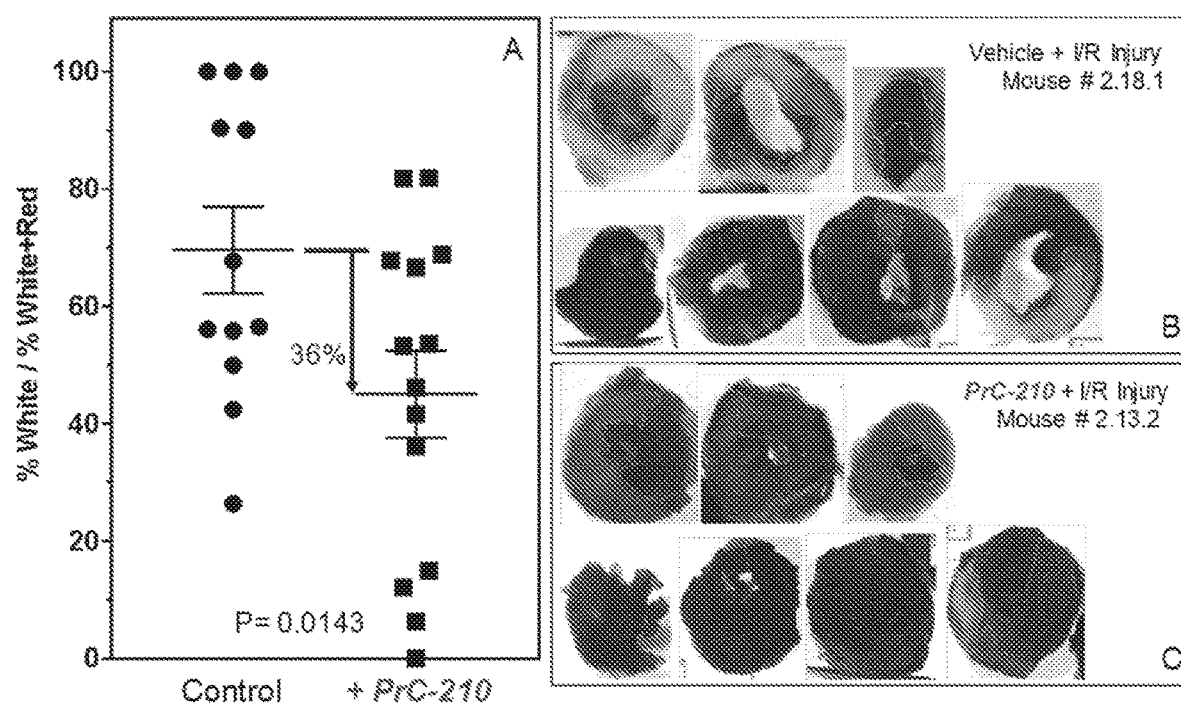
FIG. 7 shows significant reduction of cardiac muscle death in mice that receive a systemic dose of PrC-210 10 min before the left coronary artery ligation and release (after 40 min) in this mouse myocardial infarction ischemia-reperfusion model. Staining of live tissue in the hearts was done 24 hr after the coronary artery ligation-release I-R insult to the heart.

Experiments were conducted demonstrating that administering two IP injections of PrC-210 (0.252 mg/gm body weight, and 30 min later 0.05 mg/gm body weight) to mice in which the left coronary artery had been intentionally ligated (see FIG. 7) caused an average 36% reduction in the percentage of the total cardiac muscle that was stained as dead-tissue 24 hr after release of the 40 min artery ligation. The degree of cardiac muscle tissue-death caused by the surgically-induced "infarct" (40 min artery ligation) in PrC-210-injected mice was significantly less (P=0.0143) than the degree of cardiac muscle tissue-death in the mice that were injected with saline as a control.

Example 7

Figure 8:
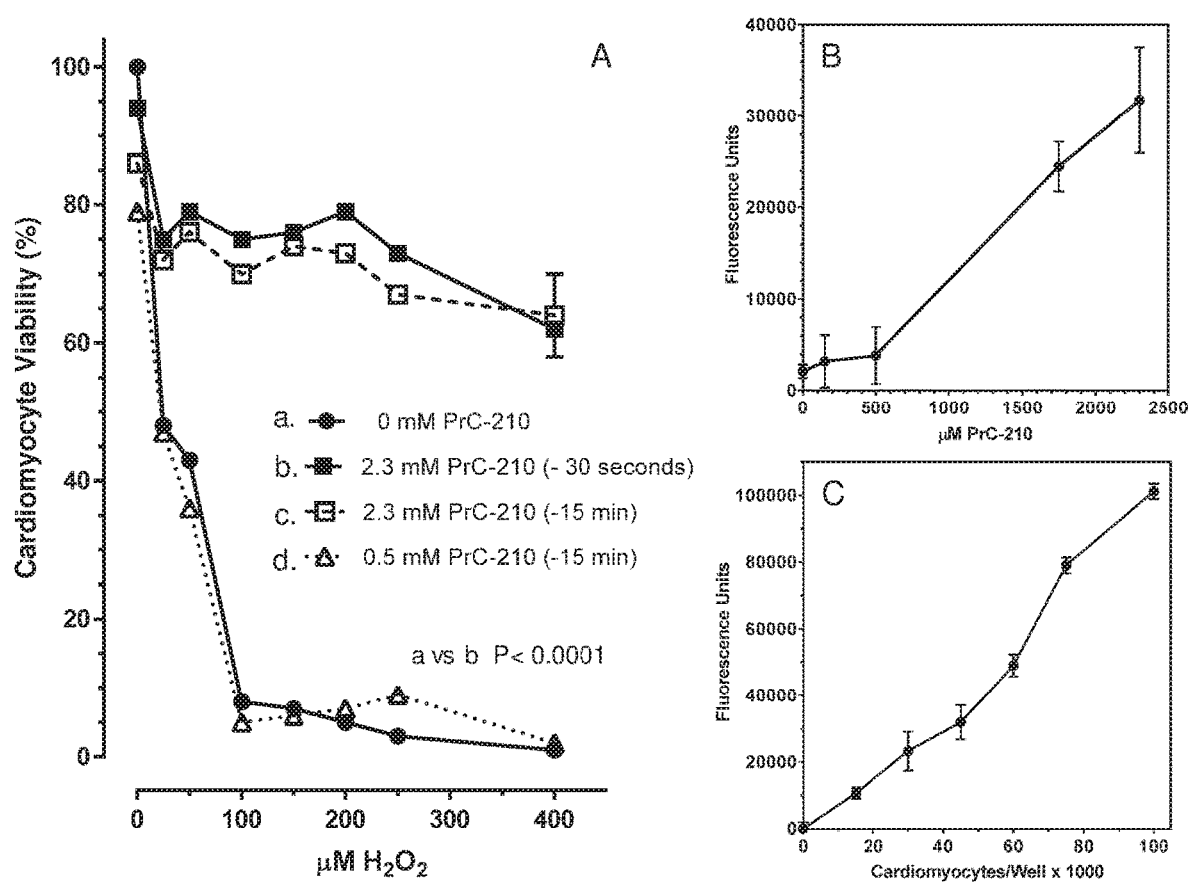
FIG. 8 shows a significant reduction of hydrogen peroxide ($H_2O_2$)-induced cardiac myocyte cell death by coincident addition of PrC-210 to the myocyte tissue culture medium.

Experiments were conducted demonstrating that addition of PrC-210 (2.3 mM) to tissue culture medium in the culture wells containing primary neonate cardiac myocytes (30,000 cells/96 well) from 3-day old mice, conferred a highly significant reduction in the myocyte cell death that was induced by adding increasing concentrations of $H_2O_2$ to the cells (see FIG. 8). In this example, addition of PrC-210 to the media either 15 min or 30 secs before the addition of $H_2O_2$ showed the same outcome in which ~80% of the $H_2O_2$-induced cell death was eliminated.

Example 8

Figure 9:
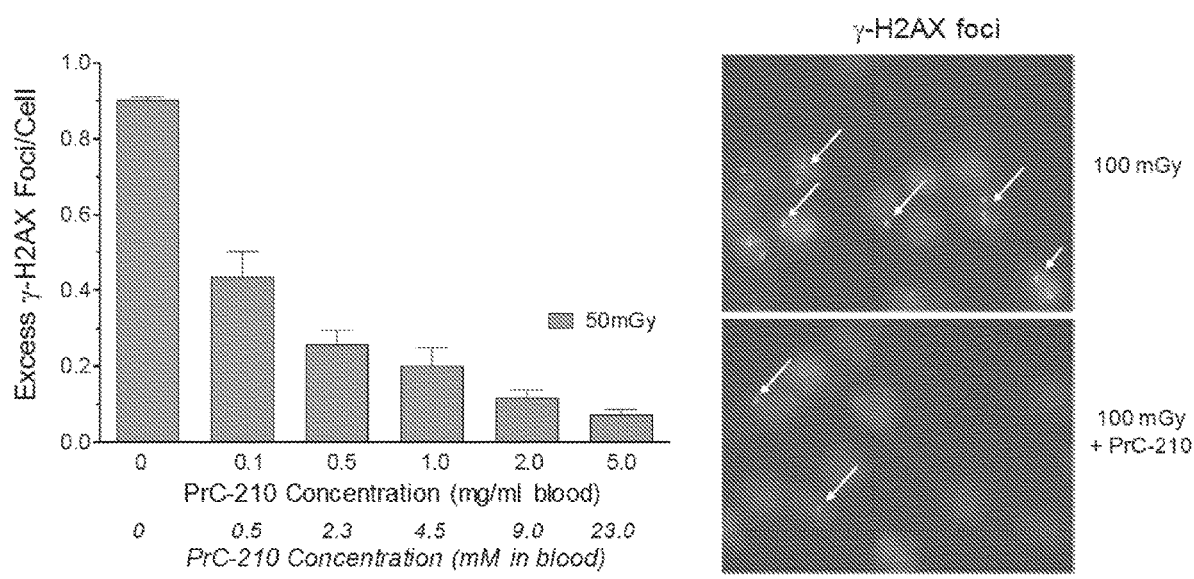
FIG. 9 shows significant PrC-210 suppression of γ-H2AX foci (i.e., ROS-induced DNA double-strand breaks) in X-ray-irradiated human blood lymphocytes. PrC-210 at the indicated concentrations (0 to 23 mM) was added to human whole blood samples 2 hr before the 100 mGy irradiation to the whole blood samples.

These experiments show highly significant PrC-210 suppression of $\gamma$-H2AX foci formation (indication of DNA double-stranded breaks) in x-ray irradiated human blood lymphocytes (FIG. 9). PrC-210 at the indicated concentrations (0 to 23 mM) was added to human whole blood samples 2 hr before the 100 mGy irradiation of the samples. Insets: Immunostaining of $\gamma$-H2AX foci (green) in human lymphocytes; nuclei were stained with 4,6-diamidino-2-phenylindole; whole blood samples were irradiated with 100 mGy x-ray 2 hr after receiving either no drug (100 mGy) or 23 mM PrC-210 (100 mGy+PrC-210).

Example 9

Experiments were conducted demonstrating (Table 3) that when rats received a single IP injection or four topical applications of the indicated aminothiols 30 min before irradiation, and then received a single x-ray dose of 17.2 Gy to a defined rectangle area of skin (1.5×3.0 cm) on their dorsal backs, radiation dermatitis was reduced. 13 days following drug application and irradiation, the severity of x-ray-induced radiodermatitis within the irradiated skin area was scored. Either dermato-topical or intraperitoneal administration of these aminothiol ROS-scavenger molecules to the rats conferred 100% suppression of radiodermatitis induced by x-ray-generated ROS during irradiation of the rat skin.

TABLE 3

Topical (or IP) aminothiol prevention of radiation-dermatitis

| Molecule Name | MW | (1) Drug Dose | | (2) Drug Application Route | n | (3) Ionizing Radiation-ROS- Induced Dermatitis (% Clear Skin[a]) |
|---|---|---|---|---|---|---|
| Vehicle | — | — | | Topical | 12 | 0% |
| PrC-210 | 148 | 370 mM (50:30:20)[b] | | Topical | 10 | 100 |
| | | 1200 mM (0:90:10)[b] | | | 4 | 100 |
| | | 200 ug/g b.w. | | IP | 2 | 100 |
| PrC-211 | 120 | 1400 mM (50:30:20)[b] | | Topical | 3 | 55 |
| | | 2200 mM (0:90:10)[b] | | | | 100 |
| | | 320 ug/g b.w. | | IP | 3 | 87 |
| PrC-252 | 105 | Expt. 1 | 300 mM | Topical | 3 | 10 |
| | | | 600 mM | | 3 | 45 |
| | | | 900 mM | | 3 | 57 |
| | | | 1800 mM | | 3 | 68 |
| | | Expt. 2 | 450 mM | Topical | 3 | 70 |
| | | 181 ug/g b.w. | | IP | 2 | 100 |
| Amifostine | 214 | 100 mM | | Topical | 4 | 0 |

[a]Percentage of irradiated skin that is clear of any scab material 13 days following 17.3 Gy radiation dose to a 1.5 cm × 3.0 cm rectangle on rat's dorsal back
[b](ethanol:propylene glycol:water)

Example 10

Figure 10:
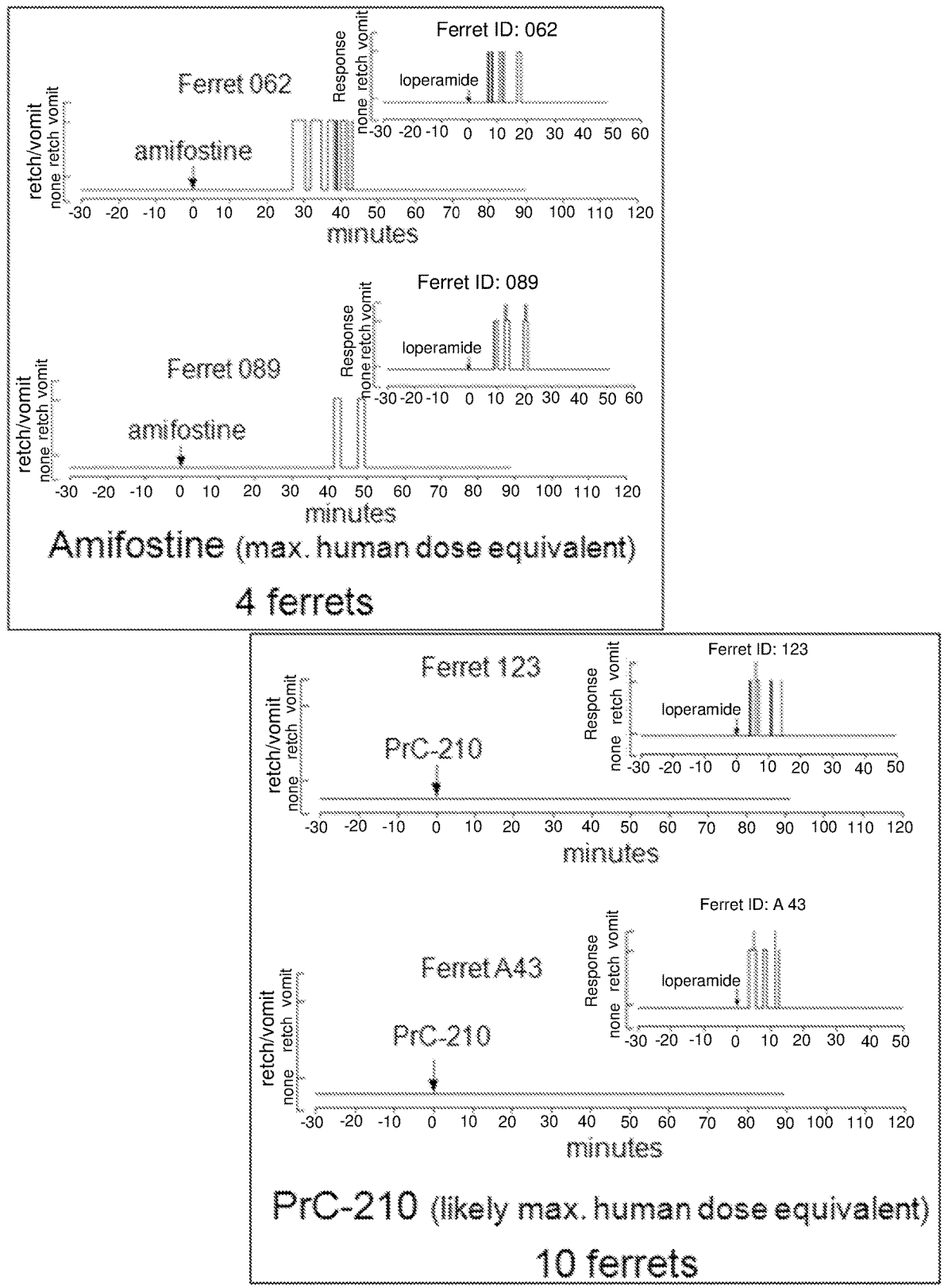
FIG. 10 (left panel) shows that amifostine induces retch and emesis responses in a ferret model; (right panel) shows that PrC-210 does not induce retch and emesis responses in a ferret model.

Experiments were conducted demonstrating that when ferrets, which had the same retch/emesis response as humans, received a subcutaneous ferret equivalent dose of the mouse 0.5 MTD dose of amifostine, that all four ferrets (data from 062 and 089 are shown here) responded with significant bouts of both retching and emesis (FIG. 10, left panel). This replicates the high incidence of nausea/emesis reported in human cases who received amifostine at the human equivalent dose of the mouse 0.5 MTD dose of amifostine.

The FIG. 10, right panel shows that when 10 ferrets received a subcutaneous ferret equivalent dose of the mouse 0.5 MTD dose of PrC-210, that none of the 10 ferrets (data from 123 and A43 are shown here) responded with any discernible retching or emesis responses.

As a positive control, with two weeks rest after the amifostine or PrC-210 challenge dose, all ferrets received a single challenge dose of loperamide, a known emetogen, and each of the 14 ferrets responded with strong retch and emesis responses. These data are shown as insets in FIG. 10.

Example 11

Figure 11:
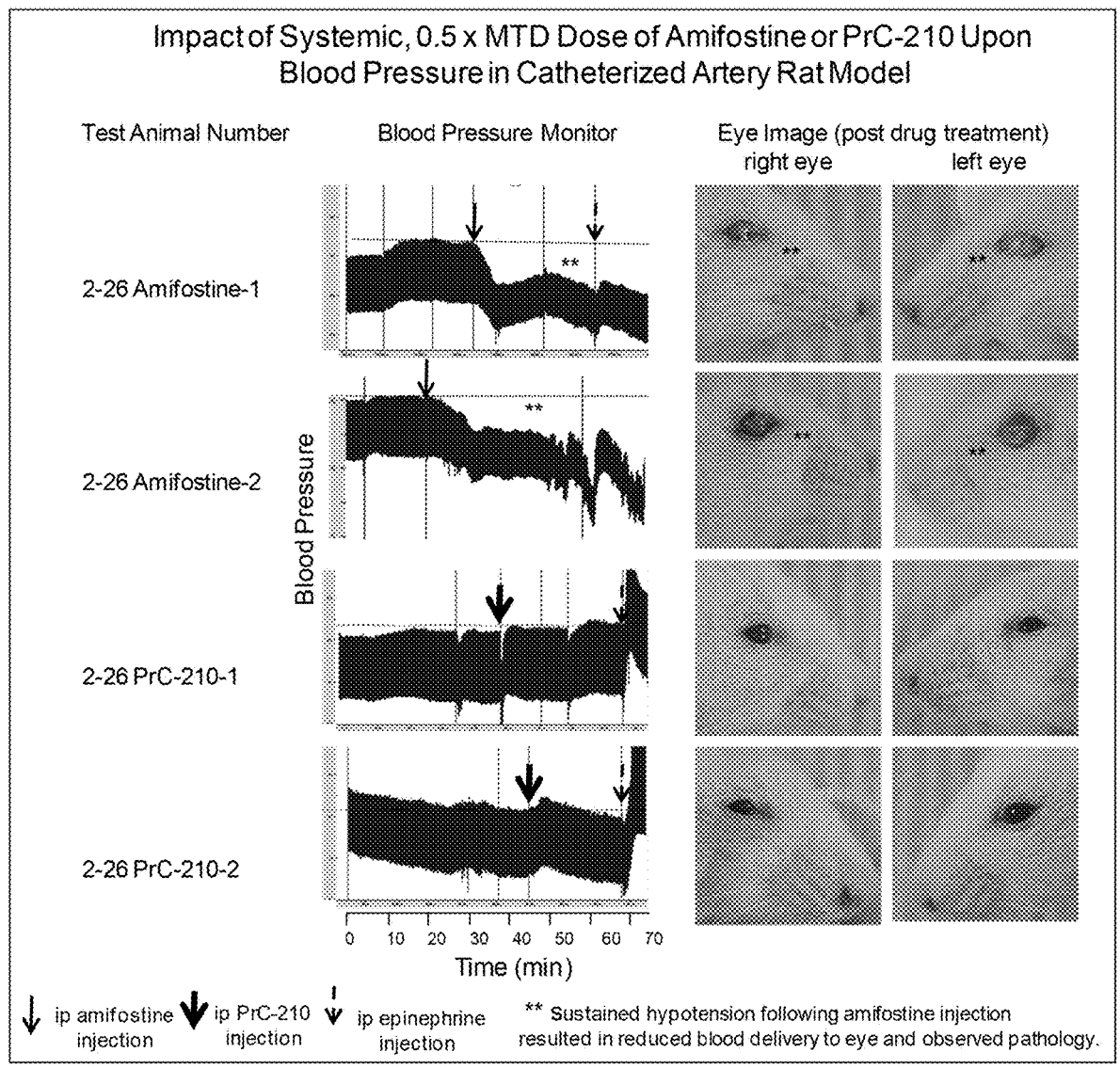
FIG. 11 shows that PrC-210 does not cause hypotension side effects. The left top panels show recorded blood pressure after administration of amifostine. The left bottom panels show recorded blood pressure after administration of PrC-210.

Experiments were conducted demonstrating that when rats with arterial catheters to measure blood pressure received a single IP dose of the rat equivalent of the mouse 0.5 MTD dose of amifostine that an immediate and irreversible drop in blood pressure occurred, and that a challenge dose of IP epinephrine had no discernible effect upon blood pressure (FIG. 11). The chronic hypotension in the rats over the recording period was associated with a discernible ocular phenotype/toxicity.

Catheterized rats that received a single IP dose of the rat equivalent of the mouse 0.5 MTD dose of PrC-210 showed no reduction in blood pressure, and a challenge dose of IP epinephrine caused a robust increase in blood pressure.

Example 12

Experiments were conducted demonstrating that PrC-210 lacked the noxious odor (i.e., sulfurous odor) associated with conventional thiol compounds. Test subjects were exposed to a solution comprising PrC-210 at the upper limit of what an approximate single human dose of PrC-210 was contemplated and a dilution series of 2-mercaptoethanol (2-ME). Each subject assigned a "smell score" to the PrC-210 by comparing the smell of the PrC-210 with the 2-ME dilutions; the smell score denotes the 2-ME dilution having a sulfurous thiol smell that most closely matched the sulfurous thiol smell of the single human dose of PrC-210. One subject assigned a smell score of 8 and the other subject assigned a smell score of 7, corresponding to 1:18,750 and 1:93,750 dilutions of 2-ME. These results show that PrC-210 at a concentration of approximately a single maximum human dose has a thiol odor that is 56,250-fold lower than 2-ME (e.g., 93,750−18,750=75,000; 75,000±2=37,500; 37,500+18,750=56,250). A 56,250-fold dilution of 2-ME is nearly odor free.

TABLE 4

| 2-ME Vial | 2-ME Fold-Dilution | Reviewer 1 PrC-210 Smell Score[A] | Reviewer 2 PrC-210 Smell Score[A] | Mean PrC-210 Smell Score |
|---|---|---|---|---|
| 1 | 1 | | | 7.5 ∴PrC-210 single maximum dose |
| 2 | 5 | | | |
| 3 | 25 | | | has thiol odor that |
| 4 | 125 | | | is 56,250-fold |
| 5 | 625 | | | lower than 2-ME |
| 6 | 3,125 | | | i.e., 93,750 − 18,750 = |
| 7 | 18,750 | | 7 | 75,000 ÷ 2 = |
| 8 | 93,750 | 8 | | 37,500 + 18,750 = |
| 9 | 468,750 | | | 56,250-fold dilution |
| 10 | 2,343,750 | | | [this is nearly odor free] |

[A] i.e., the 2-ME (2-mercaptoethanol) vial whose "thiol odor" was scored the same as the "thiol odor" from the vial of PrC-210 which contained what was calculated to be an upper limit of what a single, human PrC-210 dose might be.

Example 13

An example of a Cardioplegia Solution that is commonly used to flush a human heart, and in the process stop the heart from beating, prior to surgical manipulation of the un-beating heart in e.g., coronary bypass or valve repair surgery, includes (per liter of solution):

110 mmol sodium 16 mmol magnesium 160 mmol chloride 16 mmol potassium 1.2 mmol calcium sufficient sodium bicarbonate to achieve a pH of 7.4-7.8

Example 14

An example of an organ preservation solution, here "Belzer U W Cold Storage Solution," invented at the University of Wisconsin, which is commonly used at 4° C. to flush and maintain organs removed from donors prior to implant in the organ recipient, includes:

BELZER UW ® COLD STORAGE SOLUTION

| INGREDIENT | G/L | MMOL/L |
|---|---|---|
| Hydroxyethyl starch(Pentafraction) | 50.0 | NA |
| Lactobionic acid (as Lactone) | 35.83 | 105 |
| Potassium dihydrogen phosphate | 3.4 | 25 |
| Magnesium sulfate heptahydrate | 1.23 | 5 |
| Raffinose pentahydrate | 17.83 | 30 |
| Adenosine | 1.34 | 5 |
| Allopurinol | 0.136 | 1 |
| Total Glutathione | 0.922 | 3 |
| Pottassium hydroxide* | 5.61 | 100 |
| Sodium hydroxide/Hydrochloric acid (adjust to pH 7.4) | | |
| Water for injection q.s. | | |

Example 15

Figure 12:
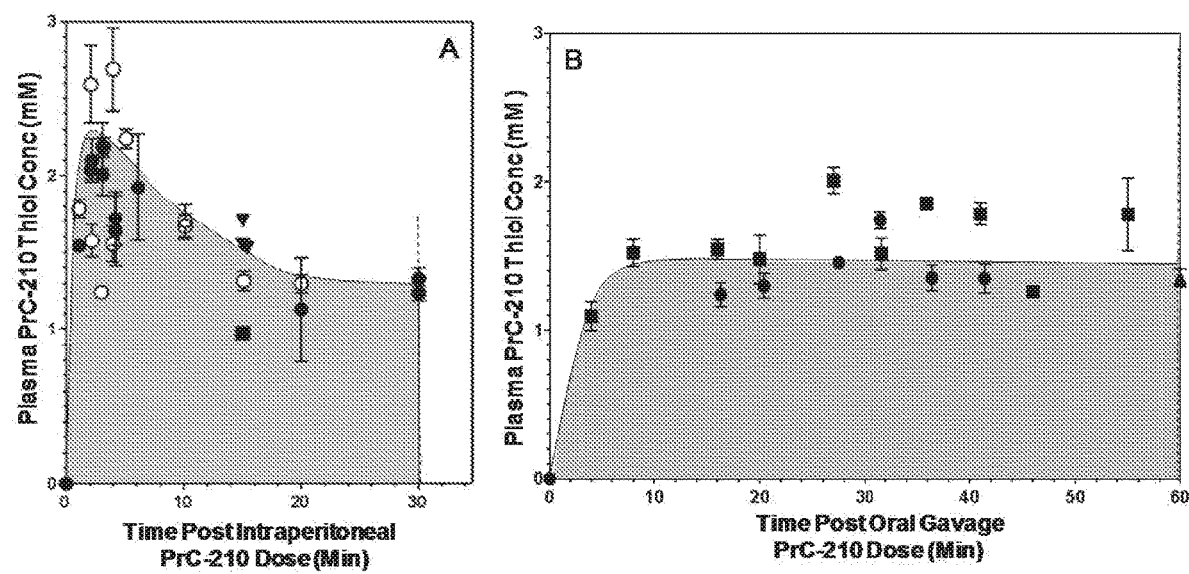
FIG. 12 shows mouse plasma levels of the active PrC-210 thiol form at various times after the molecule was administered either by (A) a single intraperitoneal injection or (B) a single oral gavage delivery to the mouse stomach.

Experiments were conducted demonstrating (FIG. 12) that when mice received a single IP injection of the 0.5 MTD IP PrC-210 dose (252 ug/gm body weight) or a single oral gavage dose of the 0.5 MTD Oral PrC-210 dose ((900 ug/gm body weight) discernible plasma levels of the active form PrC-210 thiol were measurable for extended periods afterward. Plasma concentrations of 1-3 mM PrC-210 thiol were associated with complete suppression of radiation-induced death that otherwise occurred in 100% of the vehicle-treated and irradiated mice.

Items of the Invention

1. A method of reducing or preventing ischemia-reperfusion cell death in cells which are affected by an ischemic event comprising contacting the cells with a compound having the following structure

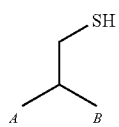
(I)

wherein A=—CH$_2$NHR' and B=—CH$_2$NHR or A=—NRR' and B=H; and wherein R and R' are independently selected from H, alkyl, and heteroalkyl, with the proviso that R and R' are not both H if B=H.

2. The method of item 1 wherein the compound is a compound having the following structure:

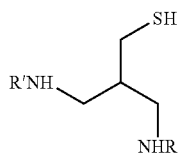

wherein R and R' are independently selected from H, alkyl, and heteroalkyl.

3. The method of item 1 wherein the compound comprises a structure according to:

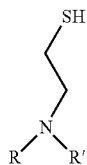

wherein R and R' are independently selected from H, alkyl, and heteroalkyl, with the proviso that R and R' are not both H.

4. The method of item 1 wherein the compound is selected from PrC-210, PrC-211, and PrC-252:

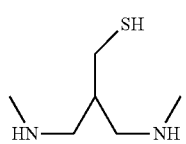
PrC-210

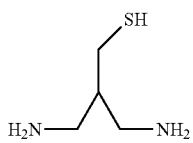
PrC-211

PrC-252

5. The method of item 1 wherein the reduction or prevention of cell death is by reduction or prevention of apoptosis.

6. The method of item 1 wherein caspase activity is reduced in cells contacted with the compound when compared to cells not contacted with the compound.

7. The method of any of the preceding items further comprising scavenging reactive oxygen species.

8. The method of any of the preceding items further providing protection to the cells' DNA against a reactive oxygen species.

9. The method of item 1 wherein the cells are part of a transplanted organ.

10. The method of item 9 wherein the cells are contacted with the compound before implantation into a recipient.

11. The method of item 9 wherein the compound is part of an organ preservation solution or a solution used for flushing an organ.

12. The method of item 9 wherein the compound is administered to the donor before and during organ removal.

13. The method of item 1 wherein systemic administration of the compound to a subject reduces or prevents ischemia-reperfusion cell death in the subject.

14. The method of item 13 wherein the compound protects the subject from ischemia-reperfusion organ toxicity.

15. The method of item 13 wherein the compound prevents ischemia-reperfusion cell death before and during reperfusion.

16. The method of item 13 wherein the subject is a transplant recipient.

17. The method of item 13 wherein the subject has suffered a heart attack or is at risk of suffering a heart attack.

18. The method of item 13 wherein the subject has suffered a stroke or is in risk of suffering a stroke.

19. The method of item 13 wherein an effective amount of the compound is administered systemically at an effective time before, during or after the ischemia-reperfusion event.

20. The method of any of the preceding items, wherein the compound is in a form of an acid-addition salt.

21. The method of item 1 wherein the cells are part of a heart perfused with a cardioplegia solution as part of the surgical manipulation of the heart.

22. The method of item 1 in which the compound is added to any flush solution that is used to protect an organ from IR injury.

23. An organ perfusion solution wherein a compound as defined in item 1 is present in a concentration of from about 1 to about 100 millimolar.

24. A unit dose of a compound as defined in item 1 that constitutes a crystalline or lyophilized powder form of an acid salt of the compound in an air-evacuated vial with a penetrable septum that enables liquid reconstitution for addition to an organ preservation solution, cardioplegia solution or to an IV bag to achieve a final concentration of the compound of 1-100 mM.

25. A cardioplegia solution wherein a compound as defined in item 1 is present in a concentration of from about 1 to about 100 millimolar.

26. A dry tablet or capsule form of a compound as defined in item 1 that enables oral delivery to a patient to achieve blood plasma concentrations of 0.5-5 mM.

REFERENCES

Abt, G., Vaghef, H., Gebhart, E., Dahlgren, C. V., and Hellman, B. The role of N-acetylcysteine as a putative radioprotective agent on X-ray-induced DNA damage as evaluated by alkaline single-cell gel electrophoresis. Mutat. Res., 384: 55-64, 1997.

Chok M K, Conti M, Almolki A, Ferlicot S, et al. Renoprotective potency of amifostine in rat renal ischaemia-reperfusion. Nephrol Dial Transplant. 2010 December; 25(12):3845-51. doi: 10.1093/ndt/gfq314. Epub 2010 Jun. 4.

Chronidou F[1], Aposthlakis E, Papapostolou I et al. Beneficial effect of the oxygen free radical scavenger amifostine (WR-2721) on spinal cord ischemia/reperfusion injury in rabbits. J Cardiothorac Surg, 2009 Sep. 17; 4:50. doi: 10.1186/1749-8090-4-50.

Kao, L. W., Kirk, M. A., Furbee, R. B., Mehta, N. H., Skinner, J. R., and Brizendine, E. J. What is the rate of adverse events after oral N-acetylcysteine administered by the intravenous route to patients with suspected acetaminophen poisoning? Ann. Emerg. Med., 42: 741-750, 2003.

Kataoka, Y., Murley, J. S., Baker, K. L., and Grdina, D. J. Relationship between phosphorylated histone H2AX formation and cell survival in human microvascular endothelial cells (HMEC) as a function of ionizing radiation exposure in the presence or absence of thiol-containing drugs. Radiat. Res., 168: 106-114, 2007.

Olsson, B., Johansson, M., Gabrielsson, J., and Bolme, P. Pharmacokinetics and bioavailability of reduced and oxidized N-acetylcysteine. Eur. J. Clin. Pharmacol., 34: 77-82, 1988.

Pakravan, N., Waring, W. S., Sharma, S., Ludlam, C., Megson, I., and Bateman, D. N. Risk factors and mechanisms of anaphylactoid reactions to acetylcysteine in acetaminophen overdose. Clin. Toxicol., 46: 697-702, 2008.

Peebles, D. D., Soref, C. M., Copp, R. R., Thunberg, A. L., and Fahl, W. E. ROS-Scavenger and radioprotective efficacy of the new PrC-210 aminothiol. Radiat. Res., 178: 57-68, 2012.

Prescott, L. Oral or intravenous N-acetylcysteine for acetaminophen poisoning? Ann. Emerg. Med., 45: 409-413, 2005.

Ryan, S. V., Carrithers, S. L., Parkinson, S. J., Skurk, C., Nuss, C., Pooler, P. M., Owen, C. S., Lefer, A. M., and Waldman, S. A. Hypotensive mechanisms of amifostine. J. Clin. Pharmacol., 36: 365-373, 1996.

Saad K R, Saad P F, Dantas Filho L, Brito J M, et al. Pulmonary impact of N-acetylcysteine in a controlled hemorrhagic shock model in rats. J Surg Res. 2013 Jun. 1; 182(1):108-15. doi: 10.1016/j.jss.2012.07.037. Epub 2012 Aug. 2.

Samuni, A. M., DeGraff, W., Cook, J. A., Krishna, M. C., Russo, A., and Mitchell, J. B. The effects of antioxidants on radiation-induced apoptosis pathways in TK6 cells. Free Radic. Biol. Med., 37: 1648-1655, 2004.

Sandilands, E. A., and Bateman, D. N. Adverse reactions associated with acetylcysteine. Clin. Toxicol., 47: 81-88, 2009.

Silva S M[1], Carbonel A A, Taha M O, Simões MJ, Montero E F. Proliferative activity in ischemia/reperfusion injury in hepatectomized mice: effect of N-acetylcysteine. Transplant Proc. 2012 October; 44(8):2321-5. doi: 10.1016/j.transproceed.2012.07.009.

Soref, C. M., Hacker, T. A., and Fahl, W. E. A new orally active, aminothiol radioprotector-free of nausea and hypotension side effects at its highest radioprotective doses. Int. J. Radiat. Oncol. Biol. Phys. 82: e701-e707, 2012.

Turkmen S, Mentese A, Karaguzel E, Karaca Y, et al. A comparison of the effects of N-acetylcysteine and ethyl pyruvate on experimental testicular ischemia-reperfusion injury. Fertil Steril. 2012 September; 98(3):626-31. doi: 10.1016/j.fertnstert.2012.05.034. Epub 2012 Jun. 19.

Wu S Z, Tao L Y, Wang J N, Xu Z Q, Wang J, Xue Y J, et al. Amifostine Pretreatment Attenuates Myocardial Ischemia/Reperfusion Injury by Inhibiting Apoptosis and Oxidative Stress. Oxid Med Cell Longev. 2017; 2017: 4130824. doi: 10.1155/2017/4130824. Epub 2017 Mar. 14.

The invention claimed is:

1. A method of reducing an ischemia-reperfusion injury (IRI) in a subject, comprising administering to said subject an effective amount of a compound PrC-210, having the following structure

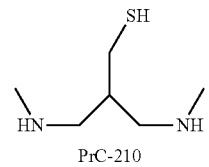

PrC-210 or a pharmaceutically acid addition salt thereof.

2. A method for reducing cell death in a tissue of a subject having suffered from an ischemia-reperfusion injury (IRI), wherein a compound PrC-210 of the formula

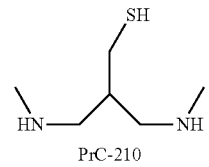

PrC-210 or a pharmaceutically acid addition salt thereof, is administered to the subject.

3. A method for reducing apoptosis in a tissue of a subject having suffered from an ischemia-reperfusion injury (IRI), wherein a compound PrC-210 of the formula

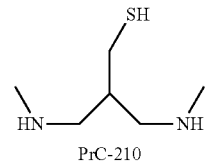

PrC-210 or a pharmaceutically acid addition salt thereof, is administered to the subject.

4. A method for reducing caspase activity in a tissue of a subject having suffered from an ischemia-reperfusion injury (IRI), wherein a compound PrC-210 of the formula

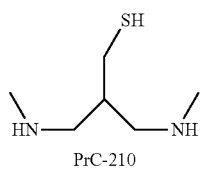
PrC-210 or a pharmaceutically acid addition salt thereof, is administered to the subject.

5. The method according to claim 1, wherein the compound PrC-210 or pharmaceutically acceptable acid addition salt thereof is administered during or before ischemia-reperfusion injury (IRI).

6. The method according to claim 1, wherein the compound PrC-210 or pharmaceutically acceptable acid addition salt thereof, is administered to a subject having a myocardial infarction or a stroke.

7. The method according to claim 1, wherein the compound PrC-210 or pharmaceutically acceptable acid addition salt thereof, is administered to a subject at risk for at least one of myocardial infarction and stroke.

8. The method according to claim 1, wherein the ischemia-reperfusion injury (IRI) occurs in a kidney of said subject.

9. The method according to claim 1, wherein the compound PrC-210 or pharmaceutically acceptable acid addition salt thereof, is administered to a subject undergoing surgery.

10. The method according to claim 9, wherein the surgery is coronary bypass surgery.

11. The method according to claim 1, wherein the compound PrC-210 or pharmaceutically acceptable acid addition salt thereof, is administered to said subject before, during or after the ischemia-reperfusion injury (IRI).

12. The method according to claim 1, wherein the compound PrC-210 or pharmaceutically acceptable acid addition salt thereof, is administered systemically at an effective time before, during or after an ischemia-reperfusion injury (IRI).

13. A method for reducing an ischemia-reperfusion injury (IRI) in a transplant organ, wherein a compound PrC-210 of the formula

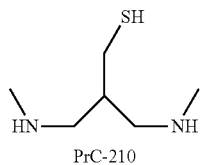
PrC-210 or pharmaceutically acceptable acid addition salt thereof, is administered to a transplant organ.

14. A method for reducing an ischemia-reperfusion injury (IRI) in a transplant organ, wherein a compound PrC-210 of the formula

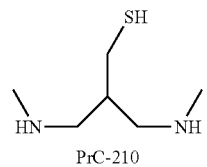
PrC-210 or pharmaceutically acceptable acid addition salt thereof, is administered to a donor of the transplant organ before organ removal from said donor.

15. A method for reducing an ischemia-reperfusion injury (IRI) in a transplant organ, wherein a compound PrC-210 of the formula

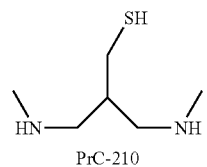
PrC-210 or pharmaceutically acceptable acid addition salt thereof, is administered to a donor of the transplant organ during organ removal from the donor.

16. A method for reducing an ischemia-reperfusion injury (IRI) in a transplant organ, wherein a compound PrC-210 of the formula

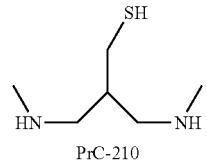
PrC-210 or pharmaceutically acceptable acid addition salt thereof is administered to a recipient of the transplant organ before or after organ transplantation.

\* \* \* \* \*